United States Patent [19]

Buysch et al.

[11] 4,181,676
[45] Jan. 1, 1980

[54] PROCESS FOR THE PREPARATION OF DIALKYL CARBONATES

[75] Inventors: Hans-Josef Buysch; Heinrich Krimm; Hans Rüdolph, all of Krefeld, Fed. Rep. of Germany

[73] Assignee: Bayer Aktiengesellschaft, Leverkusen, Fed. Rep. of Germany

[21] Appl. No.: 938,725

[22] Filed: Aug. 31, 1978

[30] Foreign Application Priority Data

Sep. 7, 1977 [DE] Fed. Rep. of Germany ....... 2740243

[51] Int. Cl.$^2$ ............................................. C07C 68/06
[52] U.S. Cl. .................................................. 260/463
[58] Field of Search ........................................ 260/463

[56] References Cited

U.S. PATENT DOCUMENTS

| | | | |
|---|---|---|---|
| 2,915,529 | 12/1959 | Bell et al. | 260/463 |
| 3,133,113 | 5/1964 | Malkemus | 260/463 |
| 3,248,414 | 4/1966 | Stevens | 260/463 |
| 3,642,858 | 2/1972 | Frevel et al. | 260/463 |
| 3,689,462 | 9/1972 | Maximovich | 260/463 |
| 3,803,201 | 4/1974 | Gilpin et al. | 260/463 |
| 3,963,586 | 6/1976 | Ginnasi et al. | 203/96 |
| 4,062,884 | 12/1977 | Romano et al. | 260/463 |

FOREIGN PATENT DOCUMENTS 2607003 8/1976 Fed. Rep. of Germany .
2615665 10/1976 Fed. Rep. of Germany .

*Primary Examiner*—Donald G. Daus
*Assistant Examiner*—M. C. Eakin
*Attorney, Agent, or Firm*—Sprung, Felfe, Horn, Lynch & Kramer

[57] ABSTRACT

An improved process for the preparation of a dialkyl carbonate by contacting a glycol carbonate with alcohol at an elevated temperature in the presence of an alkali metal or alkali metal compound, the improvement residing in employing less than 0.01 percent by weight of alkali metal and/or alkali metal compound, based upon the weight the reaction mixture.

9 Claims, No Drawings

PROCESS FOR THE PREPARATION OF DIALKYL CARBONATES

The present invention relates to a process for the preparation of dialkyl carbonates by reacting glycol carbonates with alcohols in the presence of alkali metals and/or alkali metal compounds.

The preparation of dialkyl carbonates by transesterifying alkylene carbonates with alcohols in the presence of alkali metals or alkali metal compounds is known from U.S. Pat. No. 3,642,858. The alkali metals or alkali metal compounds are used as catalysts in this process in amounts of 0.01 to 0.3% by weight, relative to the reaction mixture. Temperatures between 175° and 225° C. are given as typical reaction temperatures. According to Example 3 in the table in the U.S. Patent Specification, lower temperatures lead to low yields, even with relatively long reaction times. Side-reactions which lower the yield and make working up difficult take place, in some cases to a considerable extent, under the reaction conditions according to U.S. Pat. No. 3,642,858. Such side-reactions take place, in particular, in the case of aliphatic carbonates, which are less stable. Above all, these readily split off carbon dioxide, ethers being formed. Such side-reactions preferably take place between dialkyl carbonates and 1,2-glycols, and particularly readily between glycol carbonates and 1,2-glycols, when the proportion of glycol increases in the course of the trans-esterification. The by-products which are formed are, above all, alkyl glycol ethers and polyglycols, such as di-, tri- and tetra-glycols.

A process has now been found for the preparation of dialkyl carbonates by reacting glycol carbonates with alcohols at elevated temperature in the presence of alkali metals or alkali metal compounds, which is characterised in that less than 0.01% by weight of alkali metals and/or alkali metal compounds, relative to the reaction mixture, is employed in the reaction.

In the reaction according to the invention, it is surprising that the trans-esterification proceeds more rapidly with low amounts of alkali metals and/or alkali metal compounds than in the case of the process of the U.S. Patent Specification cited above, and that splitting off of $CO_2$ and side-reactions scarcely take place.

Compared with the state of the art, the process according to the invention has the following advantages that the amounts of catalyst are low and are only a fraction of the amount customarily used. The catalyst can therefore be separated off from the reaction mixture without difficulty and re-used. The compositions of the reaction product, caused by high amounts of catalyst, during working up of the reaction mixture by distillation are avoided in the process according to the invention. The reaction temperatures can be kept comparatively low, which saves energy costs. In spite of the low amount of catalyst, the rate of reaction is surprisingly higher than in the case of the process described in the U.S. Pat. No. 3,642,858, which gives rise to an increased space/time yield. Side-reactions, such as the polyglycol formation, are greatly suppressed and losses in yield are thereby avoided.

Starting materials for the process according to the invention are, on the one hand, aliphatic and/or cycloaliphatic hydroxy compounds with 1 to 10, preferably with 1 to 6, and particularly preferably with 1 to 4, C atoms, such as methanol, ethanol, propanol, isopropanol, n-butanol, iso-butanol, allyl alcohol, amyl alcohol, cyclohexanol, ethylcyclohexanol, benzyl alcohol and methylglycol, preferably methanol and ethanol, and on the other hand carbonates of 1,2-diols with 2 to 4 carbon atoms, such as ethylene glycol carbonate, propylene glycol carbonate, butylene glycol carbonate, vinylethylene glycol carbonate and chloromethyl-ethylene glycol carbonate; ethylene glycol carbonate and propylene glycol carbonate are particularly preferred.

The molar ratio of the reactants is not very decisive. However, an excess of alcohol of about 1 to 10 mols per mol of glycol carbonate is advisable in order to shift the equilibrium in the direction of the desired carbonate. It is, of course, also possible to employ a larger excess.

Suitable catalysts for the process according to the invention are alkali metals, such as lithium, sodium, potassium, rubidium and caesium, preferably lithium, sodium and potassium, and/or alkali metal compounds, such as the hydrides, oxides, hydroxides, alcoholates and amides, as well as the alkali metal salts of organic acids, such as acetic acid, propionic acid, butyric acid, benzoic acid and stearic acid, the alkali metal salts of carbonic acid, such as the carbonates and bicarbonates, the alkali metal salts which are derived from inorganic acids, such as hydrochloric acid, hydrobromic and hydriodic acid, nitric acid, sulphuric acid, hydrofluoric acid, phosphoric acid, hydrocyanic acid and thiocyanic acid.

The amounts of alkali metals and/or alkali metal compounds are less than 0.01% by weight. In general, they are in the range from 0.01 to 0.0001% by weight, and are preferably 0.009 to 0.0005% by weight, relative to the reaction mixture.

The reaction temperature is about 50° to 250° C., preferably 100° to 220° C. and particularly preferably 130° to 200° C.

The reaction can be carried out under normal pressure. A pressure reactor is nevertheless necessary in the case of low-boiling components if the reaction is to be carried out in the upper temperature range. The pressure is not critical. In general, the reaction is allowed to proceed under the autogenous pressure of the reactants such as develops in a closed vessel. However, one can carry out the reaction under increased pressure, for example under an inert gas atmosphere. A pressure of about 2 to 100 bars is appropriate here.

The products of the process according to the invention are suitable as solvents for cellulose derivatives and as starting materials for the preparation of diaryl carbonates and aliphatic and aromatic polycarbonates, and for medicaments and plant protection agents (compare DT-OS (German Published Specification) No. 2,528,412, DT-AS (German Published Specification) No. 1,031,512, J. Amer. Chem. Soc. 52, 314 (1930) and Ullmanns Encyklopädie d. techn. Chemie (Ullmanns Encyclopaedia of Industrial Chemistry), 3rd edition, volume 9, page 776 et seq. (1957)).

The process according to the invention is illustrated in more detail with the aid of the examples which follow, without, however, being limited to these examples.

EXAMPLE 1

A mixture of 672 g (21 mols) of methanol, 370 g (4.2 mols) of glycol carbonate and 0.09 g of sodium chloroacetate is kept at 150° C. for 2 hours. After cooling, the mixture is distilled, methanol and dimethyl carbonate first being removed under normal pressure and the higher-boiling components being removed in vacuo. In order to avoid substance losses, 2 cold traps are connected downstream of the distillation. 730 g of methanol containing 31.4% by weight of dimethyl carbonate, corresponding to 229 g of dimethyl carbonate, are obtained. This means that glycol carbonate has been converted into dimethyl carbonate to the extent of 60.5%. The higher-boiling fraction (61°–82°/0.8 mm Hg; 290 g) consists of glycol and unreacted glycol carbonate and the residue (1.0 g) consists of polyglycol. The working up losses are about 2% by weight.

COMPARISON EXAMPLE

This example is a repetition of batch 2 in the table in U.S. Patent Specification 3,642,858: a mixture of 640 g (13.9 mols) of ethanol, 264 g (3.0 mols) of glycol carbonate and 3.0 g of sodium ethylate is heated to 200° C. for 3 hours. After cooling, the mixture is worked up as in Example 1. An ethanol fraction (687 g) containing 102 g of diethyl carbonate, corresponding to a conversion of glycol carbonate to diethyl carbonate of 29%, a glycol fraction (113 g, 83°–120°/3 mm Hg) and 59 g of residue consisting of viscous polyglycols, from which the glycol fraction can be distilled out only with decomposition occurring, are obtained. The working up and substance loss (splitting off of $CO_2$) is 5% by weight. About 30% of the glycol carbonate employed has been converted into by-products.

EXAMPLE 2

A mixture of 640 g (13.9 mols) of ethanol, 264 g (3.0 mols) of glycol carbonate and 0.08 g of sodium ethylate is heated to 200° C. for 3 hours. After working up as in Example 1, an ethanol fraction containing 170 g of diethyl carbonate, corresponding to a conversion of glycol carbonate to diethyl carbonate of 48%, a glycol fraction (220 g, 62°–90°: 0.5 mm Hg) containing about 57% of glycol carbonate and 2 g of polyglycol as the residue are obtained. The working up losses are about 2% by weight. The distillation proceeds without decomposition.

EXAMPLE 3

Example 1 is repeated, but 0.05 g of sodium acetate is employed as the catalyst. Working up as in Example 1 gives the following results: the conversion of glycol carbonate to dimethyl carbonate is 65% and the distillation residue is 0.2 g, that is to say virtually no polyglycols have been formed. The yield of dimethyl carbonate is therefore almost quantitative, if working up losses of about 2% are taken into consideration.

EXAMPLE 4

Example 1 is repeated but with 0.02 g of lithium hydroxide as the catalyst. A conversion of glycol carbonate to dimethyl carbonate of 55% and 0.3 g of residue are obtained.

EXAMPLE 5

Example 1 is repeated with 0.04 g of lithium chloride as the catalyst. A conversion of glycol carbonate of 47% and 0.2 g of residue are obtained.

EXAMPLE 6

Example 1 is repeated, but 0.02 g of sodium is used as the catalyst instead of 0.09 g of sodium chloroacetate. A conversion of glycol carbonate into dimethyl carbonate of 62% and a distillation residue of 0.9 g are obtained.

EXAMPLE 7

Example 1 is repeated with a mixture of 0.01 g of lithium and 0.03 g of sodium ethylate as the catalyst.

A conversion of glycol carbonate into dimethyl carbonate of 59% and a distillation residue of 1.1 g are obtained.

EXAMPLE 8

Example 1 is repeated with 0.003 g of KOH as the catalyst.

A conversion of glycol carbonate into dimethyl carbonate of 29% and a distillation residue of 0.2 g are obtained.

EXAMPLE 9

A mixture of 576 g (18 mols) of methanol, 88 g (1 mol) of glycol carbonate and 0.025 g of sodium methylate is heated to the boil under normal pressure whilst the dimethyl carbonate/methanol azeotrope is removed via the head of a 1.7 m packed column at 63° C. After 45 hours, the transesterification has ended and 290 g of distillate, corresponding to 85.5 g of dimethyl carbonate, have been separated off.

Besides the residual methanol and the glycol formed (59.8 g), no higher glycols can be detected in the residue.

Yield of dimethyl carbonate: 95% of theory.

EXAMPLE 10

A mixture of 672 g (21 mols) of methanol, 459 g (4.5 mols) of propylene carbonate and 0.07 g of sodium is kept at 200° for 2 hours. After working up as in Example 1, it is established that 45% of the propylene carbonate employed has been converted into dimethyl carbonate. The distillation residue is 0.7 g. Thus virtually no polyglycols have been formed.

COMPARISON EXAMPLE

If experiment 10 is repeated with 1 g of sodium instead of 0.07 g, a 43% conversion of propylene carbonate into dimethyl carbonate is obtained and the distillation residue is 17 g of polyglycols.

What is claimed is:

1. In a process for the preparation of a dialkyl carbonate by contacting a glycol carbonate of a 1,2-diol having 2 to 4 carbon atoms with an alcohol selected from the group consisting of methanol, ethanol, propanol, isopropanol, n-butanol, iso-butanol, allyl alcohol, amyl alcohol, cyclohexanol, ethylcyclohexanol, benzyl alcohol and methylglycol at an elevated temperature in the presence of an alkali metal or alkali metal compound the improvement which comprises employing less than 0.01 percent by weight of alkali metal or alkali metal compound based upon the weight of the reaction mixture.

2. A process according to claim 1 wherein the alkali metal or alkali metal compound is present in an amount of 0.0005 to 0.009 percent.

3. A process according to claim 1 wherein the reaction is carried out at a temperature in the range of 50° to 250° C.

4. A process according to claim 1 wherein the reaction is carried out at a temperature in the range of 100° to 220° C.

5. A process according to claim 1 wherein the reaction is carried out in a closed vessel at autogenous pressure.

6. A process according to claim 3 wherein the process is carried out at normal pressure.

7. A process according to claim 3 wherein the process is carried out at a pressure of between 2 and 100 bars.

8. A process according to claim 1 wherein said alkali metal or alkali metal compound is a metal of lithium, sodium, potassium, rubidium or caesium.

9. A process according to claim 1 wherein an alkali metal compound is employed and the alkali metal compound is a hydride, oxide, hydroxide, alcoholate, amide or an alkali metal salt of an organic acid.

* * * * *